United States Patent [19]
Cripe

[11] Patent Number: 5,846,244
[45] Date of Patent: Dec. 8, 1998

[54] COUNTER-BALANCED OSCILLATING SURGICAL SAW

[75] Inventor: Phil Cripe, Warsaw, Ind.

[73] Assignee: Exactech, Inc., Gainesville, Fla.

[21] Appl. No.: 924,296

[22] Filed: Sep. 5, 1997

Related U.S. Application Data

[63] Continuation of Ser. No. 531,148, Sep. 18, 1995, abandoned.

[51] Int. Cl.$^6$ .................................................. A61B 17/14
[52] U.S. Cl. .............................. 606/82; 606/79; 606/169; 606/171; 606/176; 606/178; 606/183; 30/166.3
[58] Field of Search ............................... 606/79, 82, 161, 606/169, 171, 176, 178, 183; 30/165, 166.3

[56] References Cited

U.S. PATENT DOCUMENTS

| | | |
|---|---|---|
| 3,554,197 | 1/1971 | Dobbie . |
| 3,978,862 | 9/1976 | Morrison . |
| 4,625,405 | 12/1986 | Hudnutt et al. . |
| 5,016,356 | 5/1991 | Trench . |
| 5,201,749 | 4/1993 | Sachse et al. ........................... 606/177 |
| 5,263,972 | 11/1993 | Evans et al. ............................. 606/176 |
| 5,265,343 | 11/1993 | Pascaloff . |

FOREIGN PATENT DOCUMENTS

| | | | |
|---|---|---|---|
| 483135 | 7/1952 | Canada ................................. 30/166.3 |
| 322599 | 11/1934 | Italy ..................................... 30/166.3 |

OTHER PUBLICATIONS

Stryker Catalog: Powered Instrumentation for Large Bone Surgery.
3M Maxi–Driver, Air Instrument System, Procedures: One Approach.
Powered Surgical Instrument Catalog, Section F.

*Primary Examiner*—Michael Buiz
*Assistant Examiner*—Daphna Shai
*Attorney, Agent, or Firm*—Fish & Richardson P.C.

[57] ABSTRACT

A counter-balanced oscillating surgical saw for use in surgical procedures is described which greatly reduces the vibrations caused when the saw blades contact the patient's anatomy. The reduction of vibration is achieved by the present saw which uses two oscillating blades to counter the kinetic energy typically lost when only one blade is used. The preferred embodiment of the present invention includes at least two cutting blades mounted on at least two actuator blocks. The actuator blocks are preferably mounted on at least two shafts which extend from the top of the saw handle: a pivot shaft and a rotatable shaft which is rotated by an electric motor. At least two eccentric bearings are mounted to the rotatable shaft (one bearing for each actuator block) such that the bearings orbit about the rotatable shaft 180° out-of-phase with respect to one another. The actuator blocks are positioned adjacent the eccentric bearings so that they move in a reciprocating manner about the rotatable shaft of the saw. The to-and-fro motion of the actuator blocks is transformed into a counter-balanced oscillating motion of the cutting blades. Mechanical vibration, rotational and linear momentum of the saw is greatly reduced during surgery because as the cutting blades oscillate about the point of incision, the momentum produced by one cutting blade is offset by the momentum produced by its counterpart cutting blade.

16 Claims, 7 Drawing Sheets

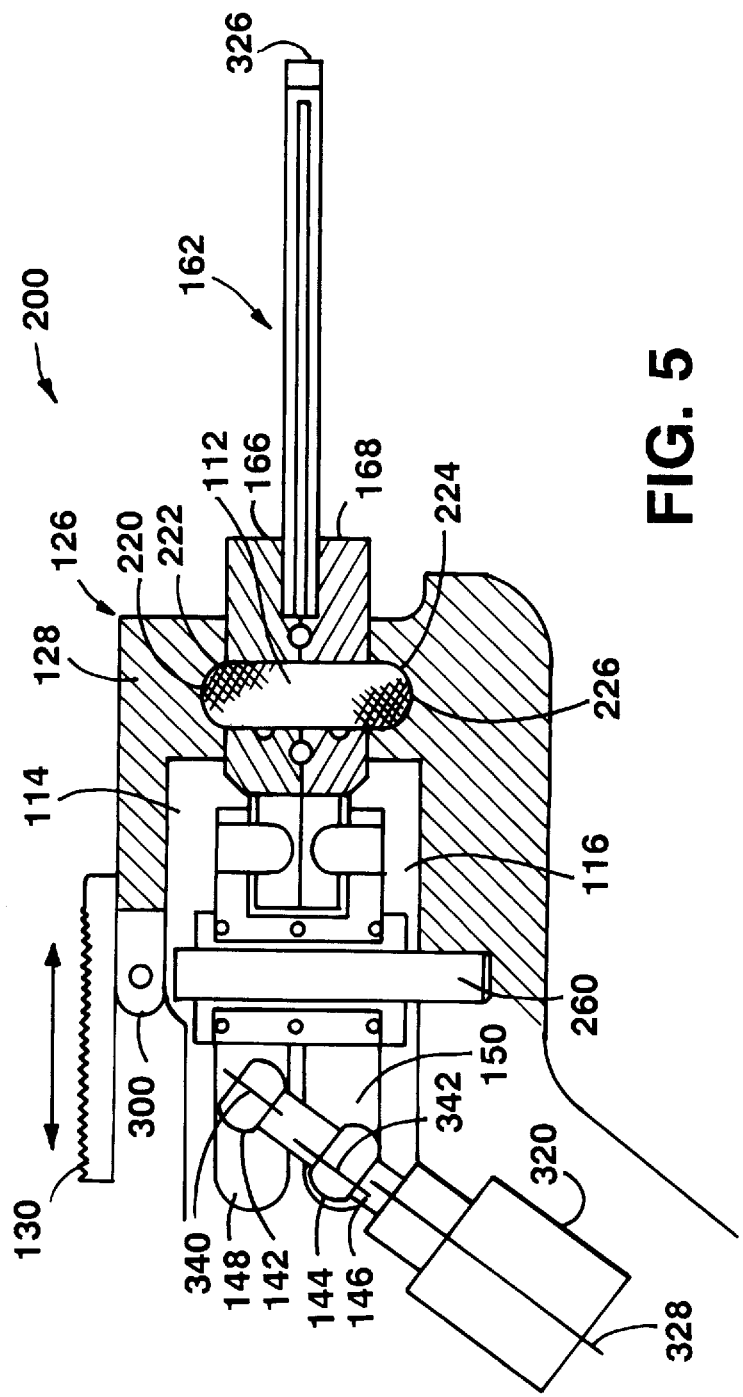

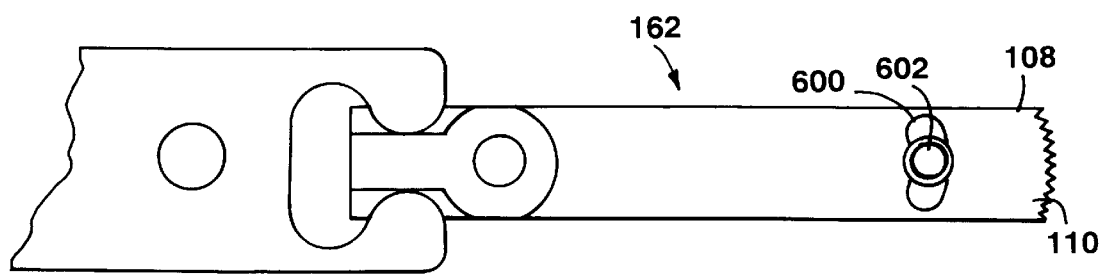
FIG. 6A
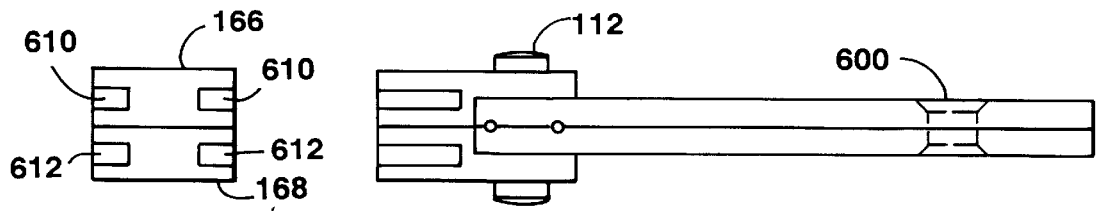
FIG. 6B  FIG. 6C
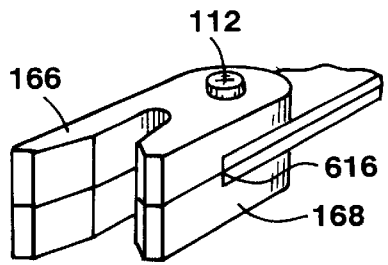
FIG. 6D

COUNTER-BALANCED OSCILLATING SURGICAL SAW

This is a continuation of application Ser. No. 08/531,148 filed On Sep. 18, 1995, now abandoned.

BACKGROUND OF THE INVENTION

1. Field of the Invention

This invention is directed to a surgical saw and, in particular, to a surgical saw having two counter-balanced surgical saw blades which reduce the amount of vibration created by the blades and thereby improve the effectiveness of the cutting action of the surgical saw.

2. Description of Related Art

In the prior art, it is known to use saws in surgery to cut through parts of a patient's anatomy. Surgical saw blades are often used in conjunction with slotted jigs or cutting blocks which may be fixed to a femur or other bone and which act as guides for the blades. The guides assist the surgeon in making precise, accurate and efficient cuts into a patient's anatomy. Accurate surgical cuts are essential for several types of surgery, especially for orthopaedic surgery. For example, surgical saw guides are essential in assisting a surgeon in preparing a patient for a total joint replacement (e.g., preparing for a total knee replacement). A distal femoral alignment guide or cutting block is typically used to align a surgical saw blade when the surgeon performs a femoral resection. Similarly, guides are employed to assist a surgeon when performing proximal tibial resections. It is therefore desirable to provide surgical saws having saw blades which can be operated within the narrow confines of such saw guides.

There are several prior surgical saws currently on the market which, for one reason or another, suffer various disadvantages and drawbacks. For example, a surgical hand piece chuck and blade is described in U.S. Pat. No. 5,263,972, to Evans, et al. The Evans surgical saw includes a single sagittal blade having a cutting part on one edge and a remote end fixed into a chuck. The remote end of the Evans blade is pushed into a slot in the chuck through a series of drop-out, safety locked-in, and fully inserted locked-in positions. The Evans surgical saw includes a provision for a surgical chuck and blade structure in which full insertion of the blade into the chuck can be accomplished rather easily. A locking means insures that a user knows whether the surgical blade is either obviously insufficiently inserted or is positively locked against escape from the surgical saw handle. In operation, the single blade taught by Evans oscillates from side to side about the incision point. The saw blade is affixed to a shaft which is at right angles to the driving shaft of the motor. Disadvantageously, the blade employed in the Evans saw has a tendency to "skive" or deflect when making incisions at an angle which is oblique to the cutting surface. The skiving or deflection of the saw blade reduces both the accuracy and effectiveness of the cutting action. The Evans saw also requires that a high rpm motor be used to drive the saw blade.

One major disadvantage of the prior art surgical saws is that they are relatively instable and therefore hinder surgeons in making precise incisions. Stable, accurate cuts are often difficult using the prior art surgical saws due to the amount of soft tissue typically proximate the incision site and the impracticality of rigidly securing or clamping the bone during the cutting process. In attempts to overcome these problems by overdriving the blade momentum relative to the cutting area, the prior art surgical saws typically operate at very high revolutions per minute. Unfortunately, when a saw is operated at very high rpms, wear on the drive motor is unduly increased. In addition, the high rpm drive motor produces loud and undesirable noise in the operating room, and also produces undesirable vibrations throughout the body of the saw. Increased saw vibration reduces the accuracy and effectiveness of the cutting action of the saw blades.

Another single blade surgical saw is described in U.S. Pat. No. 3,554,197 to Dobbie. Dobbie teaches a portable, power operated saw comprising a blade which oscillates by means of a driving motor. The motor has an output shaft which rotates about a first axis which intersects a second axis about which the single blade oscillates. Similar to the single blade surgical saw taught by Evans, the single blade saw taught by Dobbie is difficult to control when making incisions into dense material such as bone. The Dobbie blade drive motor must also operate at high rpms due to the inefficient cutting action provided by the single oscillating surgical blade. In addition, the Dobbie saw uses a spring-loaded mechanism for converting the rotary motion of the drive shaft into the oscillating motion of the blade. The spring used by Dobbie disadvantageously has a tendency to wear over a period of time, which decreases the efficiency of the blade and increases the failure rate of the saw and associated repair costs.

U.S. Pat. No. 5,016,356 to Trench discloses a saw designed to support and drive two saw blades such that the cutting edges of the saw blades travel in an orbital path about a horizontal axis. The two saw blades are mounted side by side, each blade having its proximal end mounted on eccentric shafts spaced 180° apart from each other. The Trench saw is intended for use in woodworking and similar cuts which require high speed, highly powered saws capable of producing cuts with deep kerfs. The Trench saw improves the efficiency of prior art high speed saws by having the saw teeth of the two cutting blades angularly inclined in a direction away from an apex and on opposite sides of the apex. The two saw blades are mounted in a side-by-side relationship and the saw blades are driven in orbital paths which are out-of-phase with respect to one another. By having the two saw blades arranged so that they move out-of-phase with respect to one another, a dynamic balance is achieved and vibrations of the saw are thereby reduced.

The Trench saw suffers from a number of disadvantages which makes it undesirable, especially for use in a surgical environment. For example, the saw blades do not provide the type of cutting action required in surgical procedures due to the orbital motion taken by the saw blades. The orbital motion of the saw blades tends to push the cutting surface away from the saw body and the blades, thereby reducing the effective cutting action of the saw. The reciprocating action produced by the saw blades prohibit the use of the Trench saw for the type of cuts or incisions typically required in orthopedic procedures. Also, the Trench saw is not amenable for use in surgical environments which require long, extended saw blades which are narrow enough to fit through the very narrow confines of surgical guides and jigs typically used in surgical procedures. Furthermore, the Trench saw is not easily miniaturized for use in other surgical specialties, such as hand, foot, neuro and maxillo-facial procedures. The Trench saw would require a surgeon to make incisions along the length of the saw body. Such incisions are inappropriate and nonsensical in many types of surgical settings, including but not limited to total knee replacement surgery. Moreover, the Trench saw is not amenable to being sealed for use in surgery. Therefore, there is a need for a surgical saw which is sealable, allows the use of extended and narrow surgical saw blades, decreases the vibration associated with prior art blades, and requires low rpm drive motors.

U.S. Pat. No. 4,625,405, to Hudnutt, et al teaches a saw which is typically used to cut casts from a patient's limb. The "cast cutter" employs a pair of juxtaposed, saw-edged blades which oscillate relative to each other on a common pivot point. This configuration of the saw blades uses a scissor-like cutting action resulting in a relatively wide kerf being made in the cast. The saw utilizes a patient protective blade guard which is slidable between the underside of the cast and the patient's skin. The protective blade guard is used to protect the patient during the cutting of the cast. For example, to remove the cast from the patient's leg, the cast cutter is inserted over the cast, with the protective blade guard extended between the blades and the patient's leg. The protective blade guard thereby prevents accidental contact between the cast cutter blades and the patient's leg.

Similar to the other prior art saws described above, the cast cutter saw taught by Hudnutt employs blades which are unsuitable for use in a surgical environment. For example, the cutting blades and the associated driving mechanism used to drive the blades through the cast are not amenable to being sealed for autoclaving or other forms of sterilization purposes. The Hudnutt saw is predicated on producing cuts having a wide kerf. Incisions with a wide kerf are undesirable in many types of surgery, including knee surgery. Therefore, the Hudnutt saw is not a viable alternative for use in this type of surgery. Moreover, the saw blade geometry taught by Hudnutt is incompatible for use with surgical saw guides which have openings that may be very narrowly spaced, and which consequently require long, extended blades for insertion therebetween. Moreover, the Hudnutt saw requires very high rpm drive motors, for example, drive motors which operate at approximately 20,000 rpm. As described above, high rpm saw motors introduce undesirable vibration, noise, wear and increased costs to the saw. Finally, the blades employed in the Hudnutt saw design must be held sufficiently spaced apart to avoid the heat friction which would be created by the oscillation of the blades if allowed to touch each other during operation. Because the blades taught by Hudnutt must be spaced apart to avoid heat friction energy, the blades are not amenable for use within the narrow confines of saw guides.

Other disadvantages of the prior art saws include the tendency of the saw blades to "skip", bounce, or produce a sudden impulse of energy when the blades initially make contact with a rigid surface such as a bone. Another problem with prior art saws is there tendency to "kickback" or jolt the surgeon during a restart operation. For example, if the blades of the prior art saws become lodged and stuck within the bone and the saw motor stalls, the saw handle typically experiences a sudden jolt or kickback when the surgeon restarts the saw motor. The sudden kickback can adversely affect the incision site and in some cases pose a health risk to both patient and surgeon. The problems are exaggerated in procedures on extremely delicate surgical sites such as the ear, nose or throat.

Therefore, a need exists for an improved surgical saw that requires a relatively small number of saw components, yet which can achieve effective and efficient cutting action and is lightweight and portable. Preferably, the improved saw design includes a power train and related components which are amenable to sealing for use in a surgical setting. Further, the improved surgical saw preferably allows the saw blades to be easily interchanged. By preferably allowing different families of blades to be inserted and withdrawn from the improved surgical saw, the versatility of the saw is thereby improved. Finally, there is a need for an improved surgical saw which uses counter-oscillating saw blades to reduce the vibration and motor speed requirements of the saw, and which can produce cuts having very narrow and accurate kerfs having very tight tolerances. The present invention provides such an improved surgical saw.

SUMMARY OF THE INVENTION

The present invention provides a novel counter-balanced oscillating surgical saw for use in surgical procedures. Although not limited to any particular surgical use, the present invention is advantageously used in orthopaedic surgery to assist a surgeon in preparing a patient for the implant of prosthetic devices. The present invention provides a surgical saw which allows a surgeon to quickly, accurately and efficiently cut through parts of a patient's anatomy. The present invention uses an oscillating counter-balanced blade system design which greatly reduces the amount of vibration produced during use and thereby improves the effectiveness of the cutting action of the blades and provides the surgeon greater control over the saw than is available using prior art surgical saws. The reduction of vibration is a bi-product of using two blades which counter the kinetic energy typically lost when only one blade is used.

The preferred embodiment of the present invention includes at least two cutting blades mounted on at least two actuator blocks. The actuator blocks are mounted on at least two shafts which extend from the top of the saw handle: a pivot shaft and a rotatable shaft which is rotated by an electric motor. At least two eccentric bearings are mounted to the rotatable shaft (one bearing for each actuator block) such that the bearings orbit about the rotatable shaft 180° out-of-phase with respect to one another. The actuator blocks are positioned adjacent the eccentric bearings so that they move in a reciprocating manner about the rotatable shaft of the saw. The to-and-fro motion of the actuator blocks is transformed into a counter-balanced oscillating motion of the cutting blades. Mechanical vibration, rotational and linear momentum of the saw is greatly reduced during surgery because as the cutting blades oscillate about the point of incision, the momentum produced by one cutting blade is offset by the momentum produced by its counterpart cutting blade.

The details of the preferred embodiment of the present invention are set forth in the accompanying drawings and the description below. Once the details of the invention are known, numerous additional innovations and changes will become obvious to one skilled in the art.

BRIEF DESCRIPTION OF THE DRAWINGS

FIG. 5 is a partial cross-sectional cut-away view of the surgical saw shown in FIGS. 2–4.

FIGS. 6a–6d show details of the blade cartridge assembly shown in FIGS. 4–5.

Like reference numbers and designations in the various drawings refer to like elements.

DETAILED DESCRIPTION OF THE INVENTION

Throughout this description, the preferred embodiment and examples shown should be considered as exemplars, rather than as limitations on the present invention.

Overview

Figure 1:
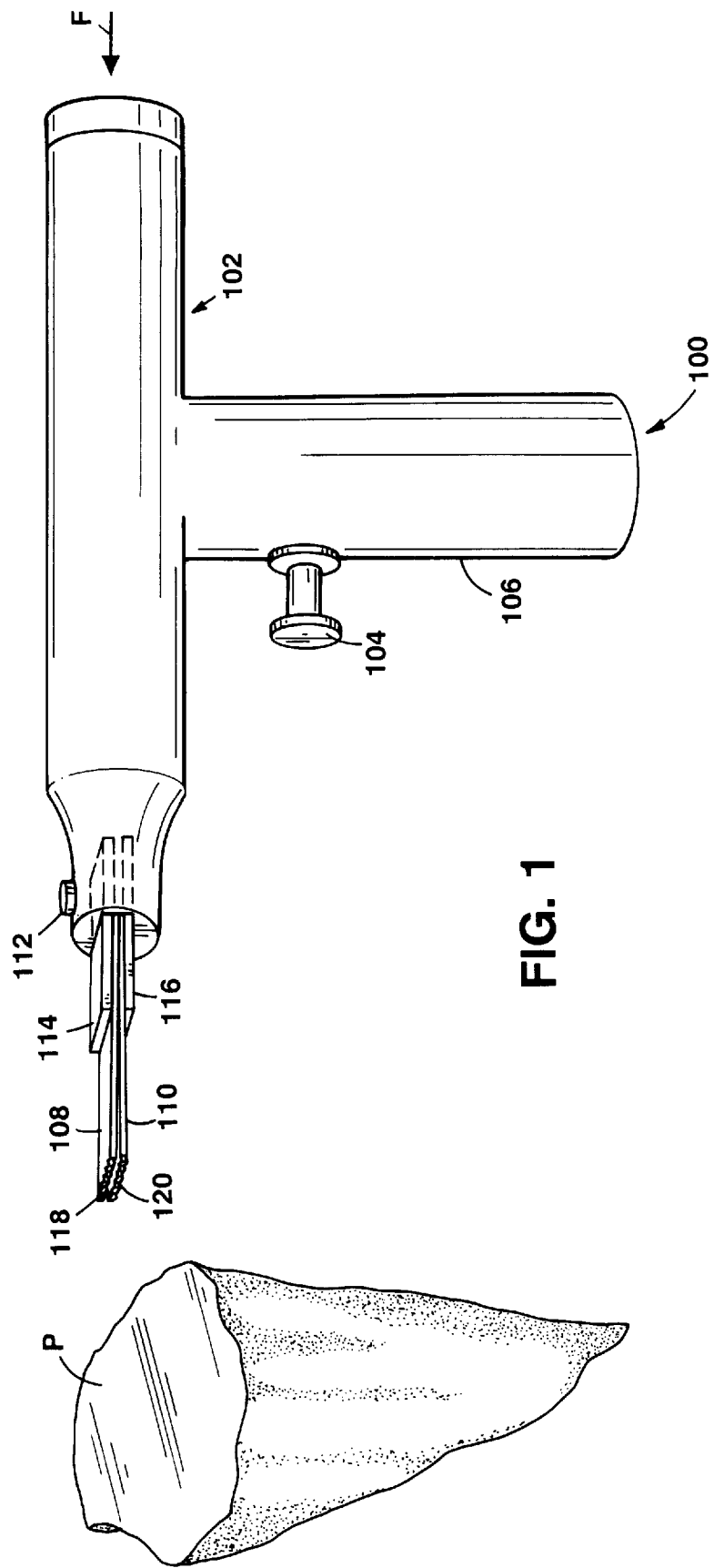
FIG. 1 is a pictorial view of a surgical saw of a type usable as a powered sagittal or oscillating saw employing the dual counter-balanced oscillating surgical saw blade system of the present invention.

FIG. 1 shows a pictorial view of a surgical saw 100 of a type usable as a powered sagittal or oscillating saw employing the dual counter-balanced oscillating surgical saw blade system of the present invention. The saw 100 may be of the type including a housing 102 which encloses a motorized drive assembly (not shown) of any convenient type. The motorized drive assembly typically includes a drive motor, powered by a power source through a switch (not shown) which is actuated by a trigger 104 mechanically coupled to the saw handle 106. In the preferred embodiment, the power source is electric, although other alternative energy sources are presently contemplated. In the illustrated embodiment, the surgical saw 100 is electrically powered using direct current from a battery power source which is enclosed within the housing 102. Optionally, the present surgical saw 100 may be powered by an external alternating current power source or an external direction current power source. In another alternative embodiment, the saw 100 is pneumatically powered using compressed gas.

As best shown in FIG. 1, the surgical saw 100 includes two oscillating cutting blades 108, 110, positioned at a distal end of a top part of the housing 102. As described below in more detail with reference to FIGS. 3–6, the blades 108 and 110 oscillate about a pivot shaft 112 which is mounted through the cutting blades 108, 110, and into the top portion of the housing 102. The blades 108, 110, are mounted onto two actuator blocks 114, 116, which reciprocate about two eccentric bearings (best shown in FIG. 3). The bearings are mounted on a drive shaft 146 (FIG. 3), which is enclosed by the housing 102. At the distal end of the blades 108, 110, the blades are serrated, forming cutting teeth 118, 120. The teeth 118, 120, are advantageously arranged to cut in both directions of a stroke of the blades 108, 110. The blades preferably comprise surgical grade stainless steel material. However, any other appropriate material may be substituted, such as titanium or ceramic.

During use, a surgeon typically holds the saw by the handle 106 which may contain batteries (i.e., if the saw is battery operated). Referring to FIG. 1, the surgeon makes an incision by applying a force ("F") in the direction of the point of incision ("P"). The incision point "P" may be on some part of a patient's anatomy, for example, on the patient's femur. The cutting teeth 118, 120, of the cutting blades 108, 110, oscillate about the point of incision "P." The momentum created by the actuator block 114 and its associated cutting blade 108 is balanced (offset) by the counter-balanced or opposite direction momentum produced by the actuator block 116 and its associated cutting blade 110. The vibration of the present surgical saw 100 is thereby greatly reduced as compared with that of the prior art surgical saws.

The present oscillating saw blade design may operate at lower drive shaft speeds than do the prior art surgical saws due to the effect of the counter-balanced oscillating cutting blades 108, 110. For example, prior art saws typically operate at approximately 20,000 rpm. In contrast, the present invention may be operated at drive motor speeds as low as approximately 4,000 rpm. Lower drive motor speeds require less power, reduce saw noise, and reduce wear on the saw motor and power source. As a result, the present surgical saw 100 is more robust, operates more quietly, and has increased durability as compared with prior art saws. Surgical cuts may be made more efficiently and more accurately by a surgeon due to the reduced vibration and increased control provided by the present surgical saw 100.

In addition, there is a reduced tendency to "skive" or bend the cutting blades when the saw is used to make incisions which are at an angle which is oblique to the starting surface. For example, as shown in FIG. 1, the cutting teeth 118, 120, cut along the force vector "F" and the blades 108, 110, do not bend or skive when they make contact with the incision point "P", even when the point "P" is at an oblique angle to the cutting force vector "F". In contrast, prior art cutting blades disadvantageously have a tendency to skive when they make contact with an incision point "P" which is not substantially at right angles to the cutting force vector "F". Further, the present invention advantageously prevents the inadvertent cutting of soft tissue because the oscillating blades 108, 110, tend to deflect soft tissue of a patient away from the cutting teeth 118, 120, of the blades 108, 110.

Figure 2:
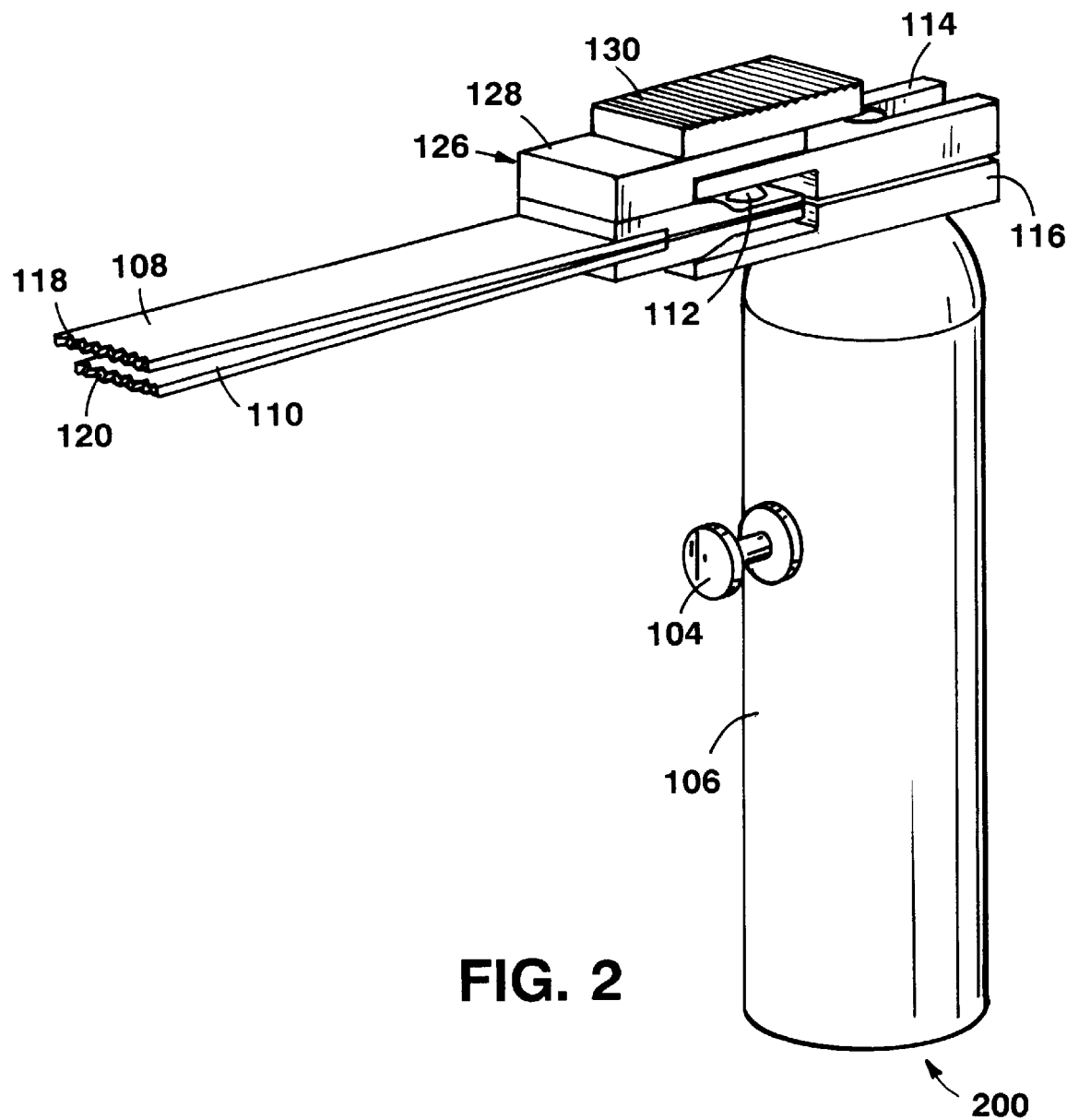
FIG. 2 is an alternative embodiment of a surgical saw employing the oscillating saw blade design shown in FIG. 1.

FIG. 2 shows an alternative embodiment of the surgical saw 200 employing the oscillating saw blade design shown in FIG. 1. Similar to the embodiment shown in FIG. 1, the alternative surgical saw includes a saw handle 106, a trigger 104, two actuator blocks 114, 116, and two oscillating blades 108, 110. The blades 108, 110, have serrated teeth 118, 120, positioned at their distal ends. As described below in more detail with reference to FIGS. 4–6, the alternative embodiment shown in FIG. 2 preferably includes a blade locking mechanism 126 comprised of a rotatable blade lock 128 and an actuator block 130. The locking mechanism is preferably positioned on top of the actuator blocks 114 and 116. As described below in more detail, the blade locking mechanism 126 advantageously allows a surgeon to quickly and easily remove and replace the cutting blades 108, 110. The blade locking mechanism 126 locks the blades 108, 110 within the surgical saw 100 after replacement of the blades for use therein.

As shown in FIG. 1 and described in more detail below with reference to FIGS. 3–6, the present invention facilitates sealing of the internal parts of the surgical saw 100, which is an essential feature for autoclaving and other forms of sterilization. Both the preferred surgical saw 100 shown in FIG. 1, and the alternative embodiment of the surgical saw 200 shown in FIG. 2, utilize a form factor which reduces the accumulation of biological debris during use. As shown in FIG. 1, everything within the housing 102 may be sealed from the external environment. For example, the motor, the power source, the internal switch, and the eccentric bearings (shown in FIGS. 3 and 4), may be sealed within the housing 102 and are thereby prevented from contaminating the surgical area. Preferably, the housing 102 is sealed using suitable liquid seals. For example, in the preferred embodiment, the seals are Teflon® or "BAL" seals available from BAL SEAL Engineering Co., Inc., located in Santa Ana, Calif. The prior art surgical saws described above, in contrast, are not amenable to being sealed, making them difficult to sterilize after use. The prior art saws generally contain many "nooks" into which biological debris may become trapped during use, making sterilization difficult and expensive.

The preferred embodiment shown in FIG. 1 and the alternative embodiment shown in FIG. 2 both consist of a small number of components. Prior art surgical saws typically required a large number of high precision and difficult to manufacture components, the increased number of components added to operational and inventory costs associated with the surgical saws. Because the present surgical saws may be manufactured using a small number of relatively low precision components, the present invention advantageously is inexpensive to manufacture, and the small number of components reduces the inventory costs associated with the surgical equipment.

DETAILS OF THE PREFERRED EMBODIMENT

Figure 3:
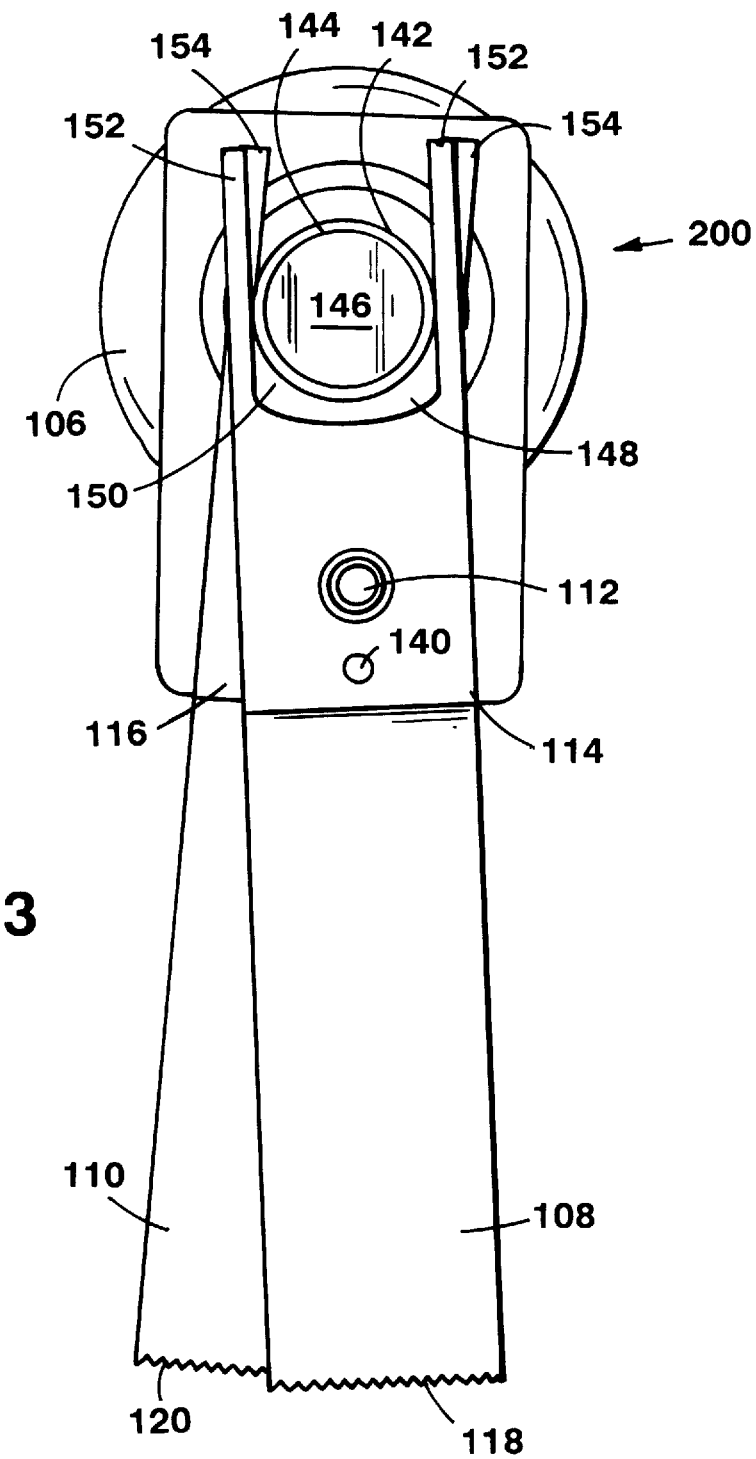
FIG. 3 is a top plan view of the surgical saw of FIG. 2.
Figure 4:
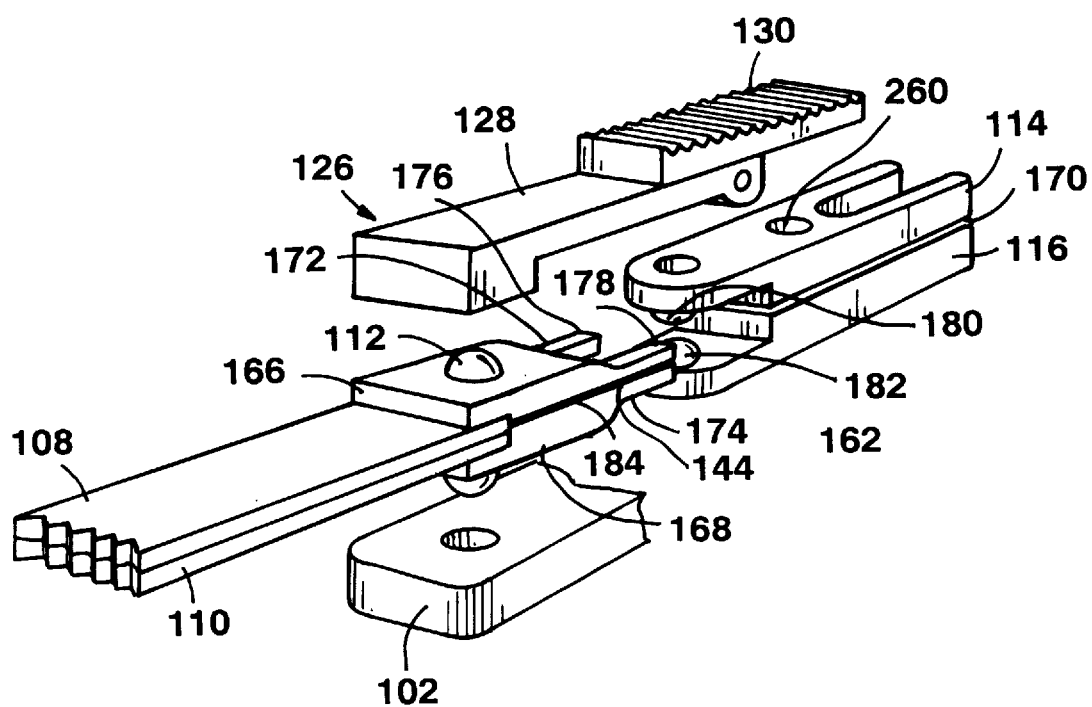
FIG. 4 is an exploded perspective view of the saw shown in FIGS. 2 and 3 showing details of the locking mechanism of the saw.

Referring now to FIGS. 3 and 4, a top plan view of the surgical saw 200 of FIG. 2 is shown. The surgical saw 200 is shown in FIG. 3 with the locking mechanism 126, the rotatable blade lock 128, and the actuator block 130 removed in order to show various components of the invention. The surgical saw 200 has two oscillating saw blades 108, 110, mounted upon two actuator blocks 114, 116, respectively. The blades 108, 110, oscillate about a pivot shaft 112. The topmost saw blade 108 is mounted to the actuator block 114 using a fastener 140. The lowermost saw blade 110 is mounted to the actuator block 116 using a similar fastener (not shown). The actuator blocks 114, 116 reciprocate about eccentric bearings 142, 144, which are mounted about the perimeter of the drive shaft 146. The rearward (topmost in FIG. 3) end of the actuator blocks 114, 116, form forks 148, 150 respectively. Each fork 148, 150, respectively, has a laterally spaced pair of rearwardly extending tines 152, 154. The tines 152, 154, snugly receive laterally therebetween the outer races of the eccentric bearings 142, 144, respectively.

More specifically, the tines 152 snugly receive laterally therebetween the outer race of the eccentric bearing 142. As the drive shaft 146 rotates, and the eccentric bearings 142, 144 orbit eccentrically about the longitudinal axis of the drive shaft 146, the bearings 142, 144 move side-to-side against the opposed faces of the tines 152 and 154. This eccentric orbiting of the bearings 142, 144 rocks the actuator blocks 114, 116 back-and-forth in an oscillatory movement relative to each other. Such back-and-forth rocking is thus in a horizontal plane and more specifically in a direction into and out of the page in FIGS. 1 and 2, and within the plane of the page in FIG. 3. Such pivotal rocking of the actuator blocks 114, 116 by the eccentrically orbiting bearings 142, 144 cause the blades 108, 110, and the blade teeth 118, 120, to oscillate horizontally within the plane of the page in FIG. 3.

The drive shaft 146 is mounted through the actuator components and engages the shaft of an electric motor (not shown) which is enclosed within the housing 106. Any suitable drive shaft and eccentric bearing which is configured to snugly receive the forks 148, 150, and the respective tines 152, 154, is contemplated by this invention.

The momentum created by the actuator block 114 and its associated blade 108 is offset and balanced by the momentum produced by the actuator block 116 and its associated blade 110. Therefore, the rotational inertia of the actuator components and surgical blades about the point of incision and along the insertion force vector is reduced by the present design. In contrast to prior art surgical saws, the dual oscillating saw blade design employed by the present invention prevents the blades from acting as a lever when they oscillate against an unstable incision surface. The cutting teeth 118, 120, are preferably designed to cut in both directions, which advantageously reduces the operating room time associated with incisions. The dual-tooth cutting action provided by the cutting teeth 118, 120 produce a stabilizing effect which enhances the cutting action of the teeth and allows a surgeon to make accurate incisions using the present invention.

Historically, prior art surgical saws have utilized high speed motors to offset the lost motion which occurs when cutting into relatively dense matter (i.e., bone matter) suspended in soft tissue matter. If it were possible to "clamp" the bone in a vice, surgical saws operating at high speeds would be desirable. However, such an operating room environment is not practical or desirable. The present invention eliminates the necessity for high speed surgical blade drive motors and provides improved cutting efficiency by taking advantage of the counter-balanced momentum produced by two oscillating surgical saws.

Referring now to FIG. 4, the components which comprise the present surgical saw 200 are shown in more detail in an exploded perspective view. FIG. 4 shows details of the locking mechanism 126, the rotatable blade lock 128, the actuator block 130, and a blade cartridge assembly 162. The locking mechanism 126 and the blade cartridge assembly 162 facilitate the insertion and removal of the dual oscillating blades 108, 110, from within the actuator blocks 114, 116.

As described in more detail below, a stationary pivot shaft 260 is mounted through each of the actuator blocks 114, 116, and into a top portion of the saw housing 102. During operation, the actuator blocks 114, 116, oscillate about the pivot shaft 260. Similarly, the two oscillating cutting blades 108, 110, oscillate about a pivot pin 112. As shown in FIG. 4, the pivot pin 112 extends through a pair of horizontally opposed blade cartridge blocks 166, 168, and downwardly into the top portion of the saw housing 102.

The pivot pin 112 has two hemispherically shaped ends. The actuator blocks 114, 116, have a pair of thrust bearings 170 inserted therebetween. The thrust bearings 170 allow the actuator blocks 114, 116, to slide against one another in a substantially frictionless manner as the actuator blocks 114, 116, oscillate about the pivot shaft 260. The actuator blocks 114, 116, are designed to slidably engage the rearward (rightmost) ends of the blade cartridge blocks 166, 168. The rearward ends of the blade cartridge blocks 166, 168, form two forks 172, 174, which have a laterally spaced pair of rearwardly extending tines. For example, the rearward (rightward) end of the blade cartridge block 166 has a laterally spaced pair of rearwardly extending tines 176, 178. The frontward (leftward) ends of the actuator blocks 114, 116, include a pair of hemispherical actuator pins 180, 182, which extend inwardly toward each other. The actuator pins 180, 182, are preferably milled to snugly slidably receive the forks 172, 174, of the blade blocks 166, 168. For example, the rearwardly facing tines 176, 178, snugly slidably receive laterally therebetween the outer race of the actuator pin 180 when the blade block 166 is manually inserted around its respective actuator block 114. The blade block 168 is similarly inserted into its respective actuator block 116 when the fork 174 is inserted around the actuator pin 182. Thus engaged, the blades 108, 110, are pivoted about the pivot pin 112 when the actuator blocks 114, 116, are actuated by their respective eccentric bearings (shown in FIGS. 3 and 5) and thereby pivoted about the pivot shaft 260.

As described above with reference to FIG. 3, the actuator blocks 114, 116 include two rearwardly facing forks 148, 150, which are designed to slidably receive two eccentric bearings (FIGS. 3 and 5). As the eccentric bearings orbit and thus effect the movement of the actuator blocks 114, 116, the actuator blocks 114, 116, pivot back and forth about the stationary pivot shaft 260. The reciprocating motion of the actuator blocks 114, 116, is transmitted to the blade cartridge blocks 166, 168, via the actuator pins 180, 182. As the actuator pins 180, 182, oscillate back and forth due to the oscillating motion of the actuator blocks 114, 116, the actuator pins 180, 182, reciprocate in a to-and-fro manner, forcing the blade blocks 166, 168, and the cutting blades 108, 110, to pivot about the pivot pin 112. Such pivoting is in a horizontal plane and more specifically in a direction in the plane of the page in FIG. 3. The blade cartridge blocks 166, 168, have thrust bearings 184 inserted therebetween. Similar to the thrust bearings 170 inserted between the actuator blocks 114, 116, the thrust bearings 184 enable the blade blocks 166, 168, to slide against one another in a substantially frictionless manner. However, any other mechanism or means for reducing such friction could be used, such as coating the contact surfaces between the blocks with Teflon® or other low friction materials.

As shown in FIG. 4, the present invention includes a locking mechanism 126 which facilitates the insertion and removal of the two cutting saw blades 108, 110. A family of different cutting blades 108, 110, and varying cutting teeth patterns 118, 120, may be used with the present invention. For example, blades may differ in thickness, width or shape, and in the mounting configurations of the blades. Although the present invention imposes no limitation on the blades thickness, the present invention typically is used with cutting blades having a thickness between 0.35 and 0.60 inch. These blade thickness ranges permit the present saw to be used with existing cutting guides.

FIG. 5 is a partial cross-sectional cut-away view of the surgical saw shown in FIGS. 2–4, showing details of the saw blade assembly and saw blade drive mechanism. As shown in FIG. 5, the locking mechanism 126 comprises a rotatable blade lock 128 and an actuator block 130. The locking mechanism 126 is shown in FIG. 5 in the engaged and locked position. The rotatable blade lock 128 includes a recess 220 shaped to accommodate a hemispherically shaped top end 222 of the pivot pin 112. As shown in FIG. 5, the pivot pin 112 has two hemispherically shaped ends: a top end 222 which is shaped to engage the recess 220, and a bottom end 224 which is shaped to engage a recess 226 formed in the saw housing 102.

To insert a saw blade for operation with the present surgical saw 200, a surgeon preferably grasps the housing 102 by the saw handle 106 with one hand, and using a thumb or index finger, grasps the top-edged portion of the actuator block 130 and slides the actuator block in a rearward (leftward) direction. The locking mechanism 126 rotates in a counter-clockwise direction about a locking mechanism pivot shaft 300 which is positioned adjacent the top end of the pivot shaft 260. As the surgeon rotates the locking mechanism 126 about the pivot shaft 300, the rotatable blade lock 128 lifts up and away from the blade block 166, causing the recess 220 to disengage the top hemispherically shaped end 222 of the pivot pin 112. Once the locking mechanism 126 and blade lock 128 are completely disengaged from the top end 222 of the pivot pin 112, the entire blade cartridge assembly 102 may be lifted out and away from the saw housing 102.

As shown in FIG. 4, the blade cartridge assembly 162 is a relatively small, compact, and easily handled unit comprised of the cutting blades 108, 110, the blade blocks 166, and the pivot pin 112. In the preferred embodiment of the present invention, the blade cartridge assembly 162 is preferably manufactured and sold as a unit. Therefore, in order to accommodate the full range of cutting blades 108, 110, which are required in the surgical art, a family of blade cartridges are contemplated for use with the present invention. Blades having varying thickness, length, shape, weight, and cutting teeth designs are contemplated.

In an alternative embodiment, the pivot pin 112 is designed to be removable by a surgeon or a technician, allowing the blades 108, 110, to be removed and sanitized after use. The blades 108, 110, in the alternative embodiment would therefore preferably comprise a high-grade surgical metal or other material (e.g., ceramic or glass) which is amenable to sterilization and re-sharpening.

Referring again to FIG. 5, the operation of the present counter-balance oscillating surgical saw 200 is now described. The saw 200 preferably has a drive motor and drive assembly 320 which includes a drive shaft 146 which extends up through the saw housing 102 and into the rearward (leftward) end of the actuator blocks 114, 116. As shown in FIG. 5, the drive assembly 320 is preferably positioned at an angle which ranges between 0° and 90° with respect to the center line 326, which is defined by the opposed mating surfaces of the actuator blocks 114, 116 and the respective blade blocks 166, 168. The drive assembly 320 is shown in FIG. 5 having its center line 328 positioned at an angle of approximately 50° from the center line 326 of the saw blades 108, 110. The upwardly facing drive shaft 146 has two spherical eccentric bearings 142, 144, mounted thereon. The center of rotation of the eccentric bearing 142 is shown as a vertical line 340, and the center of rotation of the eccentric bearing 144 is shown in FIG. 5 as a vertical line 342.

The centers of rotation 340, 342, are preferably positioned 180° apart so that when the drive shaft 146 rotates about the center line 328 of the drive shaft assembly 320, the outer races of the eccentric bearings 142, 144, reciprocate about the center line 328 in an opposite or oscillating manner. That is, when the outer race of the upper eccentric bearing 142 is at its most rightward position, the outer race of the lower eccentric bearing 144 is at its most leftward position. Conversely, when the outer race of the topmost eccentric bearing 142 is at its most leftward position, the outer race of the lower bearing 144 is at its most rightward position. Therefore, as the drive motor rotates the drive shaft 146 about the axis 328, the eccentric bearings 142, 144, move in an oscillating to-and-fro motion within the forks 148, 150 formed in the rearward (leftward) ends of the actuator blocks 114, 116. Such rocking back-and-forth of the eccentric bearings 142, 144 in a horizontal plane (i.e., in a direction into and out of the page in FIG. 5) causes the actuator blocks 114, 116, to move in a direction into and out of the page of FIG. 5.

The actuator blocks 114, 116, as described above with reference to FIGS. 3–4, pivot about the pivot shaft 260. The pivoting of the actuator blocks 114, 116, about the pivot shaft 260 is transmitted to the blade blocks 166, 168, which, in turn, causes the blade blocks 166, 168, to pivot about the pivot pin 112. Therefore, the blade blocks 166, 168, rock back-and-forth in a direction into and out of the page of FIG. 5, which in turn causes the blades 108, 110, to move in a direction into and out of the page of FIG. 5.

FIGS. 6a–6d show details of the blade cartridge assembly 162 shown in FIGS. 4–5. FIG. 6a shows a top plan view of the blade cartridge assembly 162 showing an optional blade slot 600 milled into and through the two cutting blades 108, 110. The slots are designed to snugly receive a floating pivot point 602 which provides enhanced stabilization of the cutting blades 108, 110, as they oscillate about the pivot point 602.

FIG. 6b is an end view of an optional blade cartridge assembly 162 shown from the direction of the cutting teeth 118, 120, of the cutting blades 108, 110. As shown in FIG. 6b, the blade blocks 166, 168 may optionally include blade receiving recesses 610, 612. The blade recesses 610, 612, are adapted to slidably receive the rearwardly facing tines of the blades 108, 110. In the embodiment shown in FIG. 6b, the cutting blades 108, 110, may be slidably engaged by the recesses 610, 612, by inserting the rearwardly facing tines of the cutting blades 108, 110, into the recesses 610, 612.

FIG. 6c shows details of the blade cartridge assembly 162 including the pivot pin 112 and the sliding slot 600. As shown in FIG. 6d, the blade blocks 166, 168, preferably include a plurality of thrust bearings 616 inserted therebetween. The thrust bearings 616 allow the blade blocks 166, 168, to slide against each other in a relatively frictionless manner as the blade blocks 166, 168, rotate about the pivot pin 112.

Figure 7:
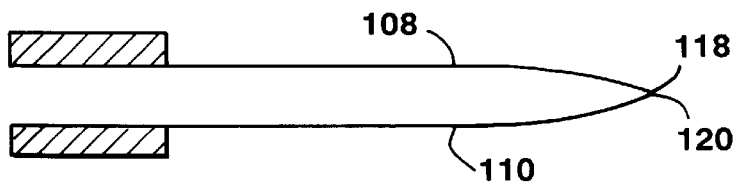
FIG. 7 shows the details of the cutting blades used in the present invention.

As shown in the insert in FIG. 7, the cutting blades 108, 110 are preferably slightly bowed in a direction toward each other to ensure that the cutting teeth 118, 120 are maintained substantially adjacent to each other during use. In the preferred embodiment, the cutting blades 108, 110, are inserted within the blade cartridge assembly 162 having a pre-loaded tension in the middle of the blades. The pre-loaded tension ensures that the cutting blades 108, 110, and more specifically, the cutting teeth 118, 120, are maintained in close proximity to each other during use.

Although not specifically shown in the figures, modifications to the preferred embodiment and other alternative embodiments of the present invention are presently contemplated. Other alternative embodiments allow the rotatable shaft to rotate at variable speeds. In another alternative of the present invention, different types of cutting blades may be employed. In another alternative embodiment, the cutting blades are detachably mounted to the actuator blades, which facilitates cleaning of the blades and saw. The blades may optionally be disposable or replaceable for sanitization purposes. In yet another embodiment, the cutting blades 108, 110 reciprocate in a direction perpendicular to the direction shown in FIGS. 1 and 2.

As described above in reference to FIGS. 1–7, the present counter-balance oscillating surgical saw allows a surgeon to make incisions more accurately due to the increased control offered by the oscillating motion of the surgical saw blades. In addition, noise levels associated with most prior art surgical saws are reduced by the design of the present invention due to the lower revolutions per minute required of the drive motor. Incisions and resections are therefore more easily and more expeditiously performed by a surgeon due to the increased cutting efficiency provided by the present invention. In addition, soft tissue typically present in orthopedic surgery is deflected by the oscillating motion of the blades 108, 110 and is therefore advantageously left intact by the present saw.

Figure 8:
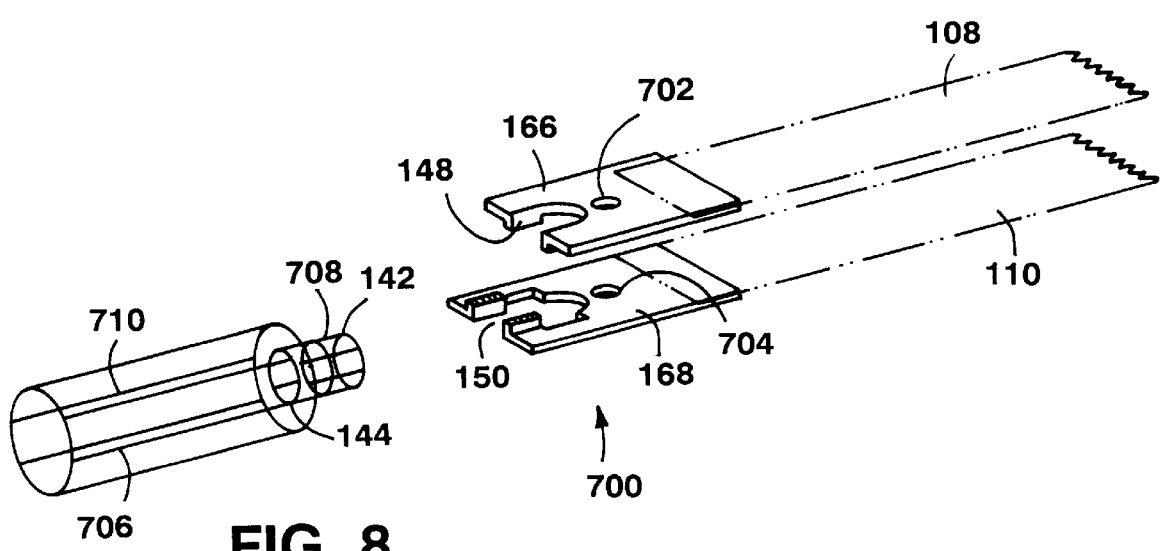
FIG. 8 shows another alternative embodiment of the present invention using an "in-line" motor housing-to-blade interface design.

FIG. 8 shows another alternative embodiment of the present invention. The surgical saw shown in FIG. 8 includes an "in-line" motor housing-to-blade interface which permits greater flexibility in adjustment of the distance from the blade pivot points to the eccentric bearings which, in turn, permits greater flexibility in adjustment of the blade excursion. The alternative embodiment 700 shown in FIG. 8 includes cutting blades 108, 110 which are secured to horizontally opposed blade cartridge blocks 166, 168. During use, the blades 108, 110 pivot about a pivot pin (e.g., pivot pin 112 shown in FIGS. 1–6) which is inserted through two pivot pin holes 702, 704. The alternative shown in FIG. 8 operates similarly to the embodiments described above with reference to FIGS. 1–6, with the exception of how the blade cartridge blocks 166, 168 interlock with a the motor housing. As shown in FIG. 8, the blade cartridge blocks 166, 168 interface with a motor housing 706 in an "in-line" manner. That is, while the embodiments of the present invention described above and shown in FIGS. 2 and 4 have blades which are substantially perpendicular with the motor shafts and the motor housings, the blades of the alternative embodiment shown in FIG. 8 operate within a parallel plane as a motor shaft 708 and the motor housing 704.

The motor shaft 708 of the alternative shown in FIG. 8 is preferably slidably received within the motor housing 706. As shown in FIG. 8, the motor housing includes a channel 710 for slidably receiving the shaft 708. The shaft 708 may be positioned within the housing 706 or extended to the position shown in FIG. 8. Furthermore, although not shown, the present invention contemplates the use of a sliding mechanism such as a key or latch which may be secured to the saw handle and is thus easily accessible to the surgeon. The sliding mechanism can assist the surgeon in establishing the extension or retraction limits for the shaft 708. Thus, the shaft 708 can be extended into any desired position by the surgeon.

The motor shaft 708 preferably includes eccentric bearings 142, 144 which rotate about the shaft 708 similar to the rotation of the eccentric bearings described above with reference to FIG. 5. That is, as the drive motor rotates the drive shaft 708, the eccentric bearings 142, 144, move in an oscillating to-and-fro motion within forks 148, 150 formed in the rearward (leftward) ends of the blade cartridge blocks 166, 168. Such rocking back-and-forth of the eccentric bearings 142, 144 in a horizontal plane (i.e., in a direction substantially into and out of the page in FIG. 8) causes the blade cartridge blocks 166, 168 to move in a direction substantially into and out of the page of FIG. 8.

By retracting the shaft 708 into the motor housing or extending the shaft 708 away from 20 the motor housing, a surgeon can easily adjust the position of the eccentric bearings 142, 144 with respect to the forks 148, 150 and the pivot pin (not shown). This adjustment changes the amount of excursion that the cutting blades take and thus affects the length of the cut that the cutting teeth make during use. Thus, the in-line blade-to-housing interface shown in FIG. 8 provides the surgeon greater flexibility and permits use of the present invention in various surgical settings and cutting conditions. For, surgeries on the spine and hands have tight tolerances which require the surgeon to make fine, accurate cuts. The in-line eccentrics saw of FIG. 8 would find great utility in such a surgical setting because it allows the surgeon to tailor the excursion made by the saw blades in very small increments simply by moving the shaft 708 into and out of the motor housing. Further, the saw shown in FIG. 8 provides even greater flexibility and enhanced utility when it is used in tandem with blades having differing configurations, thicknesses and teeth designs.

Figure 9:
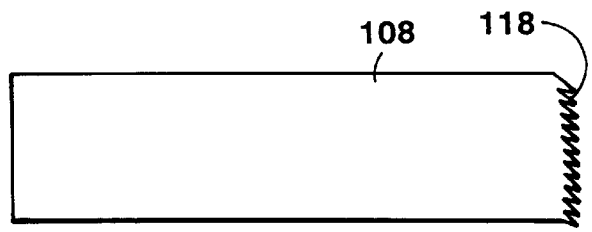
FIG. 9 shows an alternative cutting blade for use with the present invention wherein the blade has uni-directional cutting teeth designed to make a cut only when the blade moves in a first direction.

A number of embodiments of the present invention have been described. Nevertheless, it will be understood that various modifications may be made without departing from the spirit and scope of the invention. For example, although the number of embodiments have been described having only two cutting blades and actuator blocks, any number of cutting blades and blocks may be used. Also, the present invention permits the use of cutting blades which were impractical when used with the prior art surgical saws. For example, as shown in FIG. 9, the cutting blade 108 can use teeth 118 which are configured to cut in only one direction. A unidirectional cutting teeth configuration is made possible by the present invention because one blade can be used to cut in a first direction while a second blade can be used in a second opposite direction. The cutting teeth of FIG. 9 allows the blade 108 to make a cut when the blade 108 moves in a first direction, yet clean the kerf during the return stroke. Accordingly, it is to be understood that the invention is not to be limited by the specific illustrated embodiment, but only by the scope of the appended claims.

I claim:

1. A surgical saw, comprising:
   (a) a rotatable drive shaft;
   (b) a first and a second eccentric bearing coaxially mounted to the drive shaft, wherein the eccentric bearings are spaced apart from each other on the drive shaft;
   (c) a first and a second actuator block, each block having a first and a second end, wherein the first actuator block is coupled at its first end with the first eccentric bearing, and the second actuator block is coupled at its first end with the second eccentric bearing, and wherein the second end of each actuator block is adapted to be attached to a respective cutting blade; and
   (d) a pivot shaft, mounted through the first and second actuator blocks in a position between the first and second ends of the blocks, wherein, upon rotation of the drive shaft, the actuator blocks are concurrently driven about the pivot shaft in an oscillatory motion relative to each other.

2. The saw of claim 1, additionally comprising a first and a second cutting blade, each blade having a first and a second end, wherein the first ends of the cutting blades are adapted to slidably engage the second ends of the actuator blocks, and wherein the first cutting blade is slidably engaged at its first end to the second end of the first actuator block, and wherein the second cutting blade is slidably engaged at its first end to the second end of the second actuator block, and wherein, upon rotation of the drive shaft, the cutting blades are concurrently driven about the pivot shaft in an oscillatory motion relative to each other.

3. The saw of claim 2, wherein the second ends of the cutting blades have cutting edges.

4. The saw of claim 2, wherein the cutting blades are detachably engaged with the actuator blocks.

5. The saw of claim 2, wherein the first and second cutting blades are bowed in a direction toward each other such that the second ends of the cutting blades are held in close proximity toward each other during use.

6. The saw of claim 5, wherein the first and second cutting blades are pre-loaded so that the blades are biased in a direction toward each other.

7. The saw of claim 2, additionally comprising a blade locking mechanism, rotatably mounted to the actuator blocks, wherein the blade locking mechanism comprises a rotatable blade lock mounted adjacent to a lock actuator block, and wherein the rotatable blade lock holds the first ends of the first and second cutting blades in close proximity to one another within the second ends of the actuator blocks when the lock actuator block is rotated by a user into a first position, and wherein the rotatable blade lock allows the cutting blades to be removed from the actuator blocks when the lock actuator block is rotated by the user into a second position.

8. The saw of claim 1, wherein the eccentric bearings reciprocate about the axis defined by the drive shaft, and wherein the eccentric bearings reciprocate about the drive shaft 180° out-of-phase with one another.

9. The saw of claim 1, wherein the drive shaft is driven by an electric motor.

10. The saw of claim 9, wherein the electric motor operates at speeds of less than 5,000 revolutions per minute.

11. The saw of claim 1, wherein the drive shaft is driven by a pneumatic power source.

12. The saw of claim 1, additionally comprising a user selectable switch, wherein a user can place the switch in a selected one of a plurality of settings, and wherein the drive shaft rotates at a selected one of a plurality of speeds according to the switch setting selected by the user.

13. A surgical saw, comprising:
   (a) a rotatable drive shaft;
   (b) a first and a second eccentric bearing coaxially mounted to the drive shaft, wherein the eccentric bearings are spaced apart from each other on the drive shaft, and wherein the first eccentric bearing reciprocates about the drive shaft axis in an orbit which is 180° out-of-phase with the orbit reciprocated about the drive shaft by the second eccentric bearing;
   (c) a first and a second actuator block, each block having a first and a second end, wherein the first actuator block is slidably engaged at its first end with the first eccentric bearing, and the second actuator block is slidably engaged at its first end with the second eccentric bearing, and wherein the second end of each actuator block is adapted to slidably receive a respective cutting blade;
   (d) a pivot shaft, mounted through the first and second actuator blocks in a position between the first and second ends of the actuator blocks;
   (e) a first and a second cutting blade, each blade having a mounting end and a cutting end, wherein the first cutting blade is slidably engaged at its mounting end to the second end of the first actuator block, and wherein the second cutting blade is slidably engaged at its mounting end to the second end of the second actuator block; and
   (f) a pivot pin, mounted through the cutting blades in a position between the mounting ends and the cutting ends of the cutting blades, wherein, upon rotation of the drive shaft, the actuator blocks pivot back and forth about the pivot shaft, concurrently driving the blades about the pivot pin and causing the cutting ends of the blades to move in an oscillatory motion relative to each other.

14. A surgical saw, comprising:
   (a) a rotatable drive shaft;
   (b) a first and a second eccentric bearing, coaxially mounted to the drive shaft, wherein the eccentric bearings are spaced apart from each other on the drive shaft, and wherein the eccentric bearings reciprocate about the drive shaft axis in orbits which are 180° out-of-phase with one another;
   (c) a first and a second actuator block, each block having a first and a second end, wherein the first actuator block is slidably engaged at its first end with the first eccentric bearing, and the second actuator block is slidably engaged at its first end with the second eccentric bearing, and wherein the second ends of the actuator blocks are adapted to detachably receive a blade cartridge assembly;

(d) a pivot shaft, mounted through the first and second actuator blocks in a position between the first and the second ends of the actuator blocks;

(e) a blade cartridge assembly, having a first and a second end, wherein the first end is detachably mounted to the second ends of the actuator blocks, and wherein the second end of the blade cartridge assembly is adapted to slidably receive a plurality of cutting blades;

(f) a first and a second cutting blade, each blade having a mounting end and a cutting end, wherein the cutting blades are slidably engaged at their mounting ends to the second end of the blade cartridge assembly; and (g) a pivot pin, mounted through the blade cartridge assembly in a position between the first end and the second end of the assembly, wherein, upon rotation of the drive shaft, the actuator blocks rotate about the pivot shaft and the cutting blades are concurrently driven by the actuator blocks about the pivot pin in an oscillatory movement relative to each other.

15. The surgical saw of claim 14, additionally comprising:

a blade locking mechanism, positioned adjacent one end of the pivot shaft, wherein the blade locking mechanism is rotatably mounted to engage the pivot pin and the blade cartridge assembly, and wherein the blade locking mechanism holds the blade cartridge assembly within the second ends of the actuator blocks when rotated by a user into a first position, and wherein the blade locking mechanism allows the blade cartridge assembly to be removed from the actuator blocks when rotated by the user into a second position.

16. A surgical saw, comprising:

(a) a rotatable drive shaft;

(b) a first and a second eccentric bearing coaxially mounted to the drive shaft, wherein the eccentric bearings are spaced apart from each other on the drive shaft;

(c) a first and a second cutting blade, each blade having a first and a second end, wherein the first cutting blade is slidably engaged at its first end with the first eccentric bearing, and the second cutting blade is slidably engaged at its first end with the second eccentric bearing; and (d) a pivot shaft, mounted through the cutting blades in a position between the first and second ends of the blades, wherein, upon rotation of the drive shaft, the cutting blades are concurrently driven about the pivot shaft in an oscillatory motion relative to each other.

* * * * *